United States Patent [19]

Pegel et al.

[11] 4,260,603

[45] Apr. 7, 1981

[54] STEROL GLYCOSIDE WITH ACTIVITY AS PROSTAGLANDIN SYNTHETASE INHIBITOR

[76] Inventors: Karl H. Pegel, King George V Ave., Durban Natal, South Africa; Hans Walker, Lindenweg 10, 3440 Eschwege, Fed. Rep. of Germany

[21] Appl. No.: 599

[22] Filed: Jan. 2, 1979

[51] Int. Cl.³ .................... A61K 31/705; C07J 17/00
[52] U.S. Cl. .......................................... 424/182; 536/5
[58] Field of Search ............................ 424/182; 536/5

[56] References Cited

U.S. PATENT DOCUMENTS

| | | | |
|---|---|---|---|
| 3,991,186 | 11/1976 | Murai et al. | 424/182 |
| 4,083,969 | 4/1978 | Inoue et al. | 424/182 |
| 4,129,649 | 12/1978 | Inoue et al. | 424/182 |

*Primary Examiner*—Johnnie R. Brown
*Attorney, Agent, or Firm*—Cushman, Darby & Cushman

[57] ABSTRACT

Medicaments are prepared having activity as prostaglandin synthetase inhibitor comprising certain sterol glycosides, a fatty acid ester thereof or a spiroketal-steroid glucoside or fatty acid ester thereof in an amount sufficient to inhibit a prostaglandin synthetase.

31 Claims, No Drawings

STEROL GLYCOSIDE WITH ACTIVITY AS PROSTAGLANDIN SYNTHETASE INHIBITOR

BACKGROUND OF THE INVENTION

The invention relates to medicaments with prostaglandin-synthetases inhibiting activity.

Prostaglandins (PGS) are widely present in all mammalian organisms Only in recent years scientific research has made intensive efforts for extracting the biological activity of prostaglandins and acquiring knowledge thereof. According to present knowledge multiple PGS or precursors exists which vary somewhat in structure and have biological importances of wide spread occurrence, high activities and differences in metabolic action. These different actions are based on the fact that the intracellular PG synthesis can be induced by irritation or damage of cellular membranes during which in the first phase phospho-lipases release PG-precursors from membrane lipides, or that on the other hand several hormones e.g, bradykinines, acetylcholin or histamine increase the synthesis and release of PGS and that moreover PGS not only stimulate the adenyl-cylase system but the guanyl-cyclase-system also and therefore can cause an increase of intracellular APM-and GPM-concentrations.

It has already been known that the PG effects vary depending on the PG types used and the tested organs, e.g., the adenyl-cyclase is stimulated in endocrine organs by $PGE_1$ and $PGE_2$ but inhibited in fat tissue. This fact explains why PGS are able to increase or decrease the APM level in a target organ and display an adrenaline-and glycogen antagonistic effect in fat tissue. With smooth muscles PGS effect partly contractions e.g. in the uterus or intestine or dilatation e.g. in blood vessels. PGS $E_2$ and $A_2$ increase secretion of sodium and potassium in the kidney. Furthermore, it had been established already that an increase of PGS $E_2$ and $F_2$ level in the tissue can initiate and maintain inflammatory reactions.

The multiple metabolic effects of PGS are the basis for several therapeutic uses. Thus, PGS are used in the treatment of asthma and circulatory diseases because PGS of the E-type have vessel-dilatating activity. On the other hand, PGS induce labor and initiate parturition so that they possibly can be used for inducing abortion.

It was not known until recently that the activity of some medicaments with analgesic and anti-inflammatory action which had already been used for decades is based on an inhibition of the prostaglandin synthetases. This applies for e.g. acetylosalicylic acid, indometacine or ibuprofen. The strong inhibitory action of these compounds explains the activity against inflammations on the one hand and on the other hand the presence of several side effects of which only the induction of stomach hemmorrhages is referred to.

The biosynthesis of the PGS starts from membrane phospholipides which are converted into arachidonic acid and are reacted into endoperoxide-PGS by oxygen radicals. By further reactions the relatively stable PGS, thromboxanes and the relatively instable prosta-cyclin are formed of the endoperoxide-PGS.

The synthesis of $PGE_2$ and $PGF_{2\alpha}$ from arachidonic acid can be shown in a shortened way in the following formula:

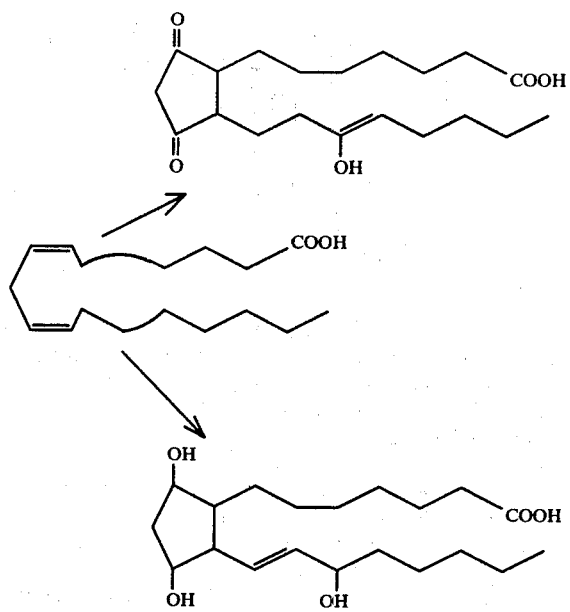

The biological residence time of PGS and their precursors is only miniscule. The decomposition starts from oxidation at C-5 and continues via the $\beta$-oxidation of fatty acids.

It has already been established that certain chemical compounds are strong PGS inhibitors. These compounds e.g. indometacine of acetylosalicylic acid had been found to be $PGE_2$-synthetase inhibitors and are used correspondingly in the treatment of rheumatic and arthritic and similar conditions for instance. The strong inhibitor action which is not necessarily restricted to $PGE_2$-synthetase leads to unwanted side effects based on this action e.g. initiations of bleedings in the stomach and intestine, other scattered bleedings, occurrence of allergies or possibilities of influencing gravidity.

Therefore, it is the object of the invention to develop a new medicament with an activity as a PGS-inhibitor which does not possess the known disadvantages.

SUMMARY OF THE INVENTION

It is proposed according to the invention to prepare medicament with an activity as PGS-inhibitor which is characterized in that it contains as the active principle sterolglycosides and/or their esters and/or spiroketal steroid glycosides and/or esters thereof. Examples of esters are the acetates.

Surprisingly and completely unexpected it has now been established that sterolglycosides, spiroketal-steroid-glycosides and esters thereof are active inhibitors for $PGE_2$-and $PGF_{2\alpha}$ synthetases without producing side effects which normally occur in influencing the PG level. Sterolins are compounds occurring frequently though only in small amounts in nature in plants and microorganisms. Sterolins are chemically glycosides of phyto-sterols including cholesterol and sterol type tetracyclic triterpenes as for example lanosterol and cycloartenol. Some of these compounds occur in various plants in relatively larger amounts, e.g. campesterol and stigmasterol and particularly sitosterol. The phytosterols correspond to the following general formula:

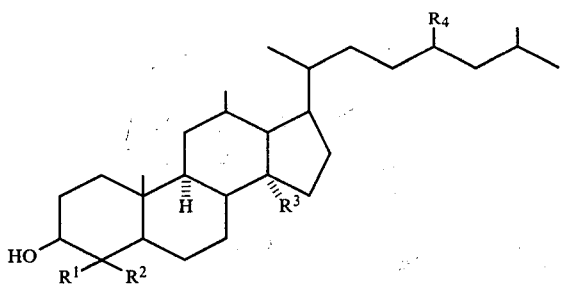

in which $R^1$, $R^2$ and $R^3$ are hydrogen atoms or methyl groups and in which $R^4$ can be a hydrogen atom or a methyl, ethyl, methylene or ethylidene group. Furthermore, there can be present double bonds at various places in the basic structure. This is true also for the side chain.

Phytosterols are present in most plants partially as steroglycosides i.e., therefore as sterolins and sometimes as their esters. The most common sterolins in nature are monoglycosides though a few diglycosides had been described as well. Besides the predominantly occurring D-glucose which is joined to the sterol by the 3-$\beta$-hydroxy group, mostly by an equatorial or $\beta$-glycoside bond, mannose, galactose, arabinose and xylose have been found in the naturally occurring compounds. As far as esters occur in nature these had been identified as esters of monobasic monocarboxylic acids, e.g., acetic acid. There can be used esters of other fatty acids, e.g., propionic acid, stearic acid. Spiroketal-steroidglycosides are those steroidsaponins which carry at the steroid basic structure—which is the aglycone—at carbon atoms 16 and 17 spiroketal group. The aglycones can be classified as being 5-ene-steroidsapogenins or 5-$\alpha$-steroidsapogenins. 5-ene-compounds are for example diosgenin, yamogenin, botogenin and correlogin while representatives of 5-$\alpha$-compounds are for example tigogenin, neotigonin, hecogenin and sisalagenin.

The nature the aglycones of the saponins exist as glycosides which carry in general 3 or more monosaccharide units in the sugar moity.

Based on this fact these compounds which are relatively rich in sugar dissolve rather readily in water and frequently give rise to a soap-like froth.

The spiroketal-steroidglycosides corresponds to the following general formula:

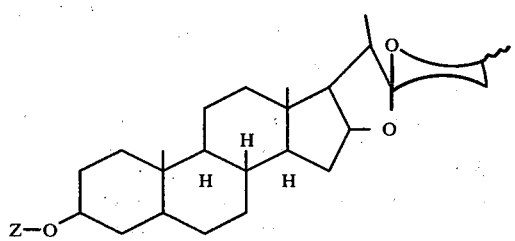

where in position 5 a double bond or an $\alpha$-hydrogen atom can be present and where Z is a mono- or disaccharide, especially glucose, which can be esterified, e.g. with acetic acid. Examples of disaccharides are maltose and lactose. Additional monosaccharides include arabinose, xylose, fructose and mannose and galactose.

The sterolins and spiroketal-steroidglycosides used according to the invention and their esters can be dispensed as extracts of plant material, enriched extracts or compounds produced synthetically.

The synthesis of the compounds can be carried out in a manner known per se as for example the know konigs-knorr-synthesis for producing glycosides using the corresponding aglycones, a C-1 brominated sugar acetate and silver oxide or silver carbonate.

In case of treatment with sterolins or their esters it is to be considered that these compounds are extremely insoluble in water. Therefore, sterolins are to be administered in an appropriate by small particle size which enables resorption. It is absolutely necessary that the sterolins used in the invention are produced and/or prepared and/or incorporated in pharmaceutical preparations in such a manner that liquid or solid solutions, emulsions or solid dispersions are formed which can be made in a known way by absorption, absorption or grinding with or without auxilliary material. All these methods lead to a reduction of particle size and crystallinity so that the compounds no longer exist as crystalline micro particles but as miniscule amorphous mono- or multilayer aggregates.

The compounds of the invention generally are used with a particle size of about 0.1 mm and preferably 0.06 mm and smaller. The same applies to the spiroketal-steroid-glycosides not-withstanding their better solubility in water. These compounds too are used with a particle size of 0.1 mm and preferably 0.06 mm or smaller.

The compounds of the invention are administered in daily doses of about 0.03 to 10 mg. The usual curing or protective dosage is about 0.1 to 0.45 mg daily. The doses can be given in 3 single doses or in a single dose with slow release of active material.

According to present knowledge the compounds are suited for treatment of diseases in which a reduction of the $PGE_2$ or $PGF_{2\alpha}$ level is necessary. Among these diseases are the following ones:

1. Ulcers, especially of the stomach and intestine,
2. endocrine disregulations,
3. urogenital diseases especially benign prostate hypertrophy and accompanying diseases,
4. heart illnesses and blood pressure disturbances,
5. edematose conditions,
6. blood vessel diseases, thrombosis varicose veins and hemorrhoids,
7. dermatitis and reactions based on excess of histamine,
8. inflammatory reactions,
9. arthritic and rheumatoid diseases,
10. allergies including asthma.

The compounds of the invention can be used in a corresponding manner to treat animal diseases. The dosage used in animal diseases can be calculated in a known manner taking 75 kg as the average human weight. The compounds can be prepared in the usual way known to the expert as pharmaceutical compositions, e.g. powders, pills, tablets, capsules, dragees, emulsions, solutions, injection—or infusion solutions, ointments or creams. The composition can comprise, consist essentially of or consist of the stated materials.

The invention will be further explained in connection with the examples.

Unless otherwise indicated all parts and percentages are by weights.

DESCRIPTION OF THE PREFERRED EMBODIMENTS

EXAMPLE 1

Production of Sitosterol-β-D-Glucoside

A mixture of 41.4 grams of sitosterol and 55.2 grams of silver carbonate in toluene were distilled with stirring until the distillate passed over free of water. Then there were dropped into the stirred, boiling mixture dropwise a solution of 82.2 grams of acetobromglucose in 100 ml of toluene. The toluene was continuously further distilled so that the total amount of water formed in the reaction was removed azeotropically. The reaction vessel was protected from light during this time. In case it is necessary, the volume of the reaction mixture is held constant by addition of dry toluene. After the addition of the bromacetoglucose solution it was held at boiling until the distillate was water free. Subsequently the reaction mixture was filtered off and the residue washed with fresh hot toluene. The united filtrate and washing liquids were then evaporated under reduced pressure. The residue was recrystallized from ethanol or hexane. The yield of sitosterol glucoside tetraacetate was 22.4 grams, corresponding to 30%.

A solution of 1 gram of sodium in 100 ml of ethanol under stirring was added quickly to a solution of 10 grams sitosterol glucoside tetracetate in 600 ml ethanol at a temperature of 45° C. The mixture was stirred for one hour whereupon 2 liters of water were added and the mixture was then stirred for another hour. The precipitated sitosterol glucoside was filtered off and washed neutral with water prior to drying it for 12 hours in a vacuum. The yield was 6.0 grams, corresponding to 95%.

By selection of suitable starting compounds all the remaining mentioned sterolins also can be produced according to the above given process.

EXAMPLE 2

Synthesis of diosgenin-3-β-D-Glucoside

A well stirred mixture of 55.2 g silver carbonate and a solution of 41/4 g diosgenin in 600 ml toluene was distilled until the collecting distillate was free of water. A solution of 82.2 g bromoacetylglucose in 100 ml toluene was then added dropwise to the stirred mixture, boiling continuing all the time with distillation in order to remove the water formed during the glucosidation reaction. At this stage the reaction vessel is protected from light and the volume of the reaction mixture is kept constant at about 500 ml by adding extra dry toluene whenever necessary. After acetobromoglucose addition has been completed, distillation is continued until no further water separates from the condensate. The reaction mixture is then filtered hot and the reside is washed with fresh, hot toluene. The combined filtrate and wash solutions are evaporated to dryness under vacuum and the residue is crystallized from ethanol or hexane. The yield of diosgenin-3-β-D glucoside tetraacetate was 25.5 g or 34.3%.

To a stirred solution of 10 g diosgenin tetraacetate in 600 ml ethanol at 45° C. is rapidly added 15 ml of an ethanolic solution of 1 g sodium in 100 ml abs. ethanol. The stirred mixture is allowed to react for 1 hour before 2 l water is added and this mixture is then stirred for a further hour. The precipitated diosgenin glucoside is then filtered off and washed to neutrality with water before it is dried under vacuum at 100° C. for 12 hours. The yield was 7 g or 90%.

Similarly the other spiroketal-steroid-glycosides mentioned above can be prepared.

EXAMPLE 3

The Preparation of Pharmaceutical Products (a) The preparation of lactose-corn starch powders incorporating diosgenin-β-D-glucoside:

A boiling hot solution of 15 g diosgenin glucoside in 2.25 l chloroform and 750 ml ethanol is mixed with 1 kg lactose powder of a particle size not exceeding 0.15 mm. The resulting slurry is dries with constant stirring and the impregnated lactose is reduced to its original particle size before it is mixed with 9 kg corn starch and 50 g magnesium stearate. Capsules are readily filled with this mixture. Thus a capsule containing 100 kg of the mixture will carry approximately 0.15 mg diosgenin-β-D-glucoside, 10 mg of lactose, 90 mg of corn starch as well as 0.5 mg of magnesium stearate.

(b) The preparation of lactose granulates containing diosgenin-β-D-glucoside:

A boiling hot solution of 5 g diosgenin glucoside in 5 l ethanol is mixed with 3.32 kg lactose of a particle size not exceeding 0.15 mm. The agitated slurry is dried and the impregnated lactose is then reduced to the original particle size before it is converted into granules of 0.7-1-2 mm particle sizes. This granulated product is also suitable for filling into capsules, where for example a capsule containing 100 mg granulate carries 0.15 mg diogenin-β-D-glucoside.

Products as described under (a) and (b) can also be prepared using the following:

(i) Glycosides of the mentioned 3-hydroxyspiroketal-steroids and especially the β-D-glucoside of tigoennin and hecogenin.

(ii) glucose, ascorbic acid or talc as carriers for the glycosides or any other inert and pharmaceutically acceptable carrier.

(iii) the contents of active glycoside in each capsule can be adjusted to any value between 0.01 and above.

(iv) the axuilliary substances described in (a) and (b) can be altered to accepted pharmaceutical practices, (v) at each stage of the production process described under (a) and (b) other pharmaceutically active substances can be added and incorporated into the final product.

(c) The preparation of tablets containing diosgenin β-D-glucoside:

A slurry, prepared by mixing 900 g lactose with a hot solution of 1.25 g diosgenin glucoside in 1 liter chloroform, is dried at room temperature and under a vacuum with constant agitation. The powdered product is then thoroughly mixed with 2.1 kg potato starch. The impregnated lactose-starch mixture is granulated by treating 250 g gelatine and 5 g glycerine. The granulate, dried under reduced pressure at room temperature is converted by known methods into 400 mg tablets. Each tablet then contains 0.15 mg diosgenin β-D-glucoside, 110.56 mg lactose, 257.97 mg potato starch, 30.31 mg gelatine and 0.61 mg glycerine.

(d) The preparation of hecogenin β-D-glucoside containing dragees:

A slurry prepared by mixing 1850 g lactose, 300 g sucrose and a hot solution of 450 mg hecogenin glucoside in 2 l chloroform is dired under a vacuum at 30° C. The powdered product is granulated by known methods by adding 1.6 l of an aqueous solution of 40 g gelatine. The granulate dried under reduced pressure at 45° C. and thoroughly mixed with 10 g magnesium stearate, is converted into 3000 pressed kernels which are finally coated to produce dragees. Every dragree then contains 0.15 mg hecogenin β-D-glucoside, 616.67 mg lactose, 100.00 mg sucrose, 13.33 mg gelatine and 3.33 mg magnesium stearate.

(e) Preparation of an ointment containing hecogenin β-D-glucoside:

To a mixture of 1 g hecogenin glucoside worked into emulsifying 90 g cetyl alcohol is added 105 g viscous paraffin and 105 g white vaseline before melting the complete mixture on a 60° C. water bath. Into this melt is stirred 699 g mater in small portions at a time. The final mixture is stirred until cold to provide an ointment containing 0.1% glucoside.

(f) Preparation of a cream containing tigogenin glucoside has been incorporated is heated to about 50° C. on a water bath. To the resulting melt 499 g water is added in small portions with constant stirring. The final cream is stirred until it reaches room temperature; during this process sufficient water is added to replace evaporation losses. This cream contains 0.1% glucoside.

Similarly the other compounds mentioned may be incorporated into pharmaceutical preparations.

EXAMPLE 4

Production of Pharmaceutically Unobjectionable Solutions (a) Solution having a content of semisynthetic Soya Sterol-β-D-Glucoside:

There was added to a boiling solution of 600 mg of semisynthetic soya sterol-β-D-glucoside in liters of absolute ethanol a solution of 10 grams of polyvinyl pyrrolidone in 4 liters of distilled water having a temperature of 65° C. The cooled 60% ethanolic solution was filled into 250 ml flasks. The patients were directed to receive one-half teaspoon corresponding to 2.5 ml of this mixture 3 times a day.

The total solution yielded 40 250 ml flasks, each of which held about 100 doses of 2.5 ml and therefore was sufficient for a treatment of about 33 days. Each teaspoon having a content of 2.5 ml had a content of 0.15 mg sterolins, 2.5 mg PBP and 1.5 ml ethanol.

It should be observed that concentrations of over 0.075 mg of sterolins and 1 mg of PVP for each 100 ml of 60% aqueous ethanol should not be exceeded if clear solutions are desired, i.e., that about 0.1875 mg of sterolins per 2.5 ml of aqueous 60% ethanol is the maximum dose for a clear solution.

According to the described process there can also be produced solutions of sterol monoglycosides or monoglucosides. Of course, all of these compounds have low solubilities so that these solutions according to the described methods should not be exposed to low temperatures to prevent turbidity.

(b) Solutions containing semisynthetic sitosterol-β-D-Maltoside.

800 mg of sitosterol-β-D-maltoside were dissolved in a mixture of 3 liters of ethanol and 7 liters of water at gentle reflux. The cooled 30% aqueous ethanol solution was then filled into 250 ml flasks. The patients were directed to receive 2.5 ml of this solution 3 times daily (according to the size thereof one-half or an entire teaspoon full).

The total solution yielded 40 250 ml flasks, each of which held about 100 doses of 2.5 ml, so that the total amount was sufficient for a treatment of about 33 days. 2.5 ml of the solution contained 0.2 mg sterolins and 0.75 ml of ethanol.

According to the described process there can also be produced solutions of other sterol disaccharides. The water solubility of the β-D-maltoside, the β-D-lactoside, and the β-D-cellobioside of sitosterol are respectively 0.38 mg, 0.21 mg and 0.75 mg per ml of water at a temperature of 24° C. This solubility is above the preferred individual doses employed of the compounds.

The preferred individual dose employed for sterol disaccharides is 0.2 mg, or 0.6 mg per day(for 3 doses).

It is therefore indicated that other pharmaceutically eeefective compounds can also be worked into the solutions together with the sterol disaccharides. Furthermore, the alcohol content of these sterolin solutions can be changed; in a give case also other pharmaceutically unobjectionable solvents can be used. Furthermore, there can also be used pure water as the sole solvent.

According to the described method the spiroketal-steroidglycosides can also be worked up into pharmaceutically acceptable solutions.

EXAMPLE 5

Pharmacological testing of sterolins and spiroketalsteroidglycosides (a) Toxicity testing of sterolins In the testing of the acute toxicity with rate, mice rabbits, dogs and primates by oral administration e.g., sitosterol-β-D-glucoside even in doses of 1 to 2 grams/kg of body weight no toxic effects were ascertained. Also, in administration over a long period of time of daily doses of 100 to 200 mg/kg of body weight with these animal species there could be detected toxicity and also no gout-like appearances so that the tolerance can be designated as good.

EXAMPLE 6

Proof of activity as PGS inhibitor

The activity of the compounds as PGS inhibitor was proved according to the method described by A. L. Willis. Conditions of trial are described for example in Proceedings of a Workshop held during the VIIIth European Dermatology Congress Helsinki 1975.

Siliconized cuvettes of the aggregometer are used at a temperature of 37° as incubation vessels in which an arachidonate solution was rapidly stirred with a PG synthetase enzyme system, usually from sheep vesicular gland. To this solution in the cuvette there is added anticoagulated plateletrich plasma, previously warmed to 37° C. Light transmission through the cuvette was recorded immediately after addition. The comparison sample showed a significant peak in the platelet aggregation after 45 seconds of incubation time which proved the formation of $PGE_2$ and $PGF_{2\alpha}$ and the corresponding platelet aggregation.

In the test samples containing 0.00001% sterolglycoside or spiroketal-steroidglycoside no platelet aggregation occurred. This clearly shows that the formation of PGs via endo-peroxide compounds from arachidonate was inhibited.

EXAMPLE 7

It had previously been established that PGS, $PGE_2$ and $PGF_{2\alpha}$ as well as the endoperoxide precursors plan an important role in the initiating of rheumatoid arthritis. Therefore, the activity of the compounds of the invention as PGS inhibitors had been tested in pharmacological trials.

When comparing arthritis based on experimental erysipeloid of for example rats with human rheumatic arthritis an extensive correspondence of the morphological changes can be observed. The tests had been made according to the publication of Schulz et al. Beitr. Path. 154, 1–26, 27–51 (1975). The arthritis of rats caused by erysipeloid can be reproduced with nearly 100 percent effectiveness with a single injection. In case of arthritis caused by erysipeloid always more than 6 joints of the limbs are transformed, namely big and small joints of the limbs in the same manner. With experimental erysipeloid all animals exhibit extensively proliferative transformations even after 3 months.

In the test of the compounds the following parameters of the manifestation phase had been used for estimating the activity of the compound.

Paw volume

The arthritis of rats is characterized in animals with a body weight of 150 g after the third day, with a body weight of 200 g after the 5th day by an extensive periarticular edema.

Kidney (protein secrection)

Nephroses caused by microthrombes can occur in 30 to 40 percent of the animals during the 7$^{th}$ to 8$^{th}$ day.

Eye

Inflammations of the cornea (turbidity) about 8$^{th}$ day.

External genitals, tip of tail

Necroses caused by thrombes about 6$^{th}$ to 8$^{th}$ day.

Aorta

With rats fibrine-rich thrombes occur about 6$^{th}$ to 11$^{th}$ day of the intima of the aorta. The largest space covered is about 8$^{th}$ day.

Male wistar rats with a body weight of 150 to 180 g were used for the tests. The animals had been kept in single cages and got a rat standard diet (Ssniff R) and water ad libitum.

The room temperature was constantly 22° C, the relative air humidity 50–60%. The daily illumination time was 12 hours.

Prior to the beginning of the tests the animals had an acclimatization period of 10 days.

The infection was carried out with the erysipeloid strain T 28. The dosage was 2 ml s.c. (about 100–200 millions germs). The compounds to be tested had been suspended in sterile saline solution and had been injected i.p. in a dosage of 5 mg/kg body weight. The treatment was 5 times per week from infection day to end of test or death of animal.

The evaluation of the characterizing aorta thrombes showed the following results:
  comparison group: value 2.80
  sitosterolglucoside: 2.00
  hecogeninglucoside: 1.38
  diosgeninglucoside: 1.33.

What is claimed is:

1. A medicament with activity as a prostaglandin synthetase inhibitor comprising a pharmaceutically acceptable carrier and an effective amount to act as a prostaglandin synthetase inhibitor of a sterol glycoside which is a glycoside of tall oil sterols, sitosterol, ergosterol, cholesterol, 5α-cholesterol, lanosterol, 24,25-dihydrolanosterol, stigmasterol, sitoor soybean sterols or a fatty acid ester of such a sterol glycoside or a spiroketal-steroid glycoside which is a glycoside of diosgenin, hecogenin, tigogenin, yamogenin, botogenin, correlogin neotiogonin or sisalagenin or a fatty acid ester of such a spiroketal-steroid glycoside.

2. Medicament according to claim 1 containing the glucosides of tall oil sterols, sitosterol, ergosterol, cholesterol, 5α-cholesterol, lanosterol, 24,25-dihydrolanosterol, stigmasterol or soybean sterols.

3. Medicament according to claim 1 containing a β-D-galactoside, β-D-maltoside, β-D-lactoside, β-D-glucoside of sitasterol or β-D-cellobioside of sitosterol.

4. Medicament according to claim 1 containing a glucoside of diosgenin, hecogenin or tigogenin, 5. Medicament according to claim 1 containing the active substance with a particle size of less than 0.1 mm diameter.

6. Medicament according to claim 3 wherein the active substance has particle size of less than 0.06 mm diameter.

7. A method of inhibiting a prostaglandinsynthetase in a mammal comprising administering to the mammal a composition according to claim 1 in an amount effective to inhibit the prostaglandin-synthetase.

8. A method according to claim 7 wherein when an ester is employed it is an ester of acetic acid, propionic acid, or stearic acid.

9. A method according to claim 7 wherein the compound is a glucoside of tall oil sterols, sitosterol, ergosterol, cholesterol, 5α-cholesterol, lanosterol, 25,25 dihydrolanosterol, stigmasterol or soybean sterols.

10. A method according to claim 7 wherein the compound is a β-D-galactoside, β-D-maltoside, β-D-lactoside or β-D-cellobioside of sitosterol.

11. A method according to claim 7 wherein the compound is a glucoside of diosgenin, hecogenin, or tigogenin.

12. A method according to claim 7 in which the compound is administered in an amount sufficient to reduce the PGE$_2$ level.

13. A method according to claim 7 in which the compound is administered in an amount sufficient to reduce the PGF$_{2α}$ level.

14. A medicament according to claim 1 wherein when the ester is employed it is an ester of acetic acid, propionic acid or stearic acid.

15. A medicament according to claim 14 wherein when the ester is employed it is an ester of acetic acid.

16. A medicament according to claim 1 wherein the ester employed is an ester of a fatty acid having 2 to 18 carbon atoms.

17. A method according to claim 7 wherein the ester employed is an ester of a fatty acid having 2 to 18 carbon atoms.

18. A medicament according to claim 16 containing about 0.03 to 10 mg of the glycoside.

19. A medicament according to claim 18 containing 0.1 to 0.45 mg of the glycoside.

20. A medicament according to claim 1 containing about 0.03 to 10 mg of the glycoside.

21. A medicament according to claim 20 containing 0.1 to 0.45 mg of the glycoside.

22. A medicament according to claim 14 containing about 0.03 to 10 mg of the glycoside.

23. A medicament according to claim 22 containing about 0.1 to 0.45 mg of the glycoside.

24. A method according to claim 7 wherein the medicament is administered daily in an amount of about 0.03 to 10 mg of the glycoside.

25. A method according to claim 24 wherein the medicament is administered daily in an amount of 0.1 to 0.45 mg of the glycoside.

26. A method according to claim 17 wherein the medicament is administered daily in an amount of about 0.03 to 10 mg of the glycoside.

27. A method according to claim 26 wherein the medicament is administered daily in an amount of about 0.1 to 0.45 mg of the glycoside.

28. A method according to claim 8 wherein the medicament is administered daily in an amount of about 0.03 to 10 mg of the glycoside.

29. A method according to claim 28 wherein the medicament is administered daily in an amount of about 0.1 to 0.45 mg of the glycoside.

30. A method according to claim 24 wherein the medicament is free from the fatty acid ester of the spiorketal steroid glycoside.

31. A medicament according to claim 20 which is free from the fatty acid ester of the spiroketal steroid glycoside.

* * * * *